US00PP36868P2

(12) United States Plant Patent
van Noort

(10) Patent No.: US PP36,868 P2
(45) Date of Patent: Jul. 29, 2025

(54) ***GERANIUM* PLANT NAMED 'MVNG1905'**

(50) Latin Name: *Geranium sanguineum*
Varietal Denomination: MVNG1905

(71) Applicant: Marco van Noort, Warmond (NL)

(72) Inventor: Marco van Noort, Warmond (NL)

(73) Assignee: MARCO VAN NOORT BREEDING B.V., Warmond (NL)

( * ) Notice: Subject to any disclaimer, the term of this patent is extended or adjusted under 35 U.S.C. 154(b) by 0 days.

(21) Appl. No.: 19/048,920

(22) Filed: Feb. 8, 2025

(51) Int. Cl.
*A01H 5/02* (2018.01)
*A01H 6/42* (2018.01)

(52) U.S. Cl.
USPC ..... Plt./324

(58) Field of Classification Search
USPC ..... Plt./324
See application file for complete search history.

*Primary Examiner* — Susan McCormick Ewoldt
(74) *Attorney, Agent, or Firm* — Penny J. Aguirre

(57) ABSTRACT

A new cultivar of *Geranium sanguineum* plant named, 'MVNG1905', characterized by its flowers that are relatively large in size that open pink and change to violet-purple in color, its re-blooming throughout the season, its long flowering season that commences early in the season, and its broadly spreading and slightly upright plant habit.

1 Drawing Sheet

Botanical classification: *Geranium sanguineum.*
Cultivar designation: 'MVNG1905'.

CROSS-REFERENCE TO RELATED APPLICATIONS

This application is related to a European plant breeders' rights application filed on Sep. 8, 2023, application No. 2023/1862. The Information for the Plant Breeders' Rights Application was received directly from the Inventor. This application is also co-pending with a U.S. Plant Patent Applications filed for plants derived from the same breeding program that are entitled *Geranium* Plant Named 'MVNG1811' (U.S. Plant Patent pending application Ser. No. 19/048,917) and *Geranium* Plant Named 'MVNG1901' (U.S. Plant Patent pending application Ser. No. 19/048,919).

BACKGROUND OF THE INVENTION

The present invention relates to a new and distinct cultivar of *Geranium* plant, botanically known as *Geranium sanguineum* 'MVNG1905' and will be referred to hereafter by its cultivar name, 'MVNG1905'. 'MVNG1905' is a new cultivar of herbaceous perennial grown for use as a garden plant.

'MVNG1905' arose from an on going breeding program conducted by the Inventor in Warmond, The Netherlands. The objectives of the breeding program is to develop new cultivars of *Geranium* that have healthy growth habits, re-blooming habits, and resistance to higher temperatures in dryer locations.

'MVNG1905' originated as a seedling that arose from seed planted from open pollination of an unnamed and unpatented plant of *Geranium sanguineum* in May of 2020. The male parent is therefore unknown. 'MVNG1905' was selected as a single unique plant in June of 2021 from the resulting seedlings.

Asexual propagation of the new cultivar was first accomplished by stem cuttings under the direction of the Inventor in Warmond, The Netherlands in December of 2023. Asexual propagation by stem cuttings and tissue culture tissue culture using meristematic tissue has determined that the characteristics of the new cultivar are stable and are reproduced true to type in successive generations.

SUMMARY OF THE INVENTION

The following traits have been repeatedly observed and represent the characteristics of 'MVNG1905'. These attributes in combination distinguish 'MVNG1905' as a new and distinct cultivar of *Geranium.*

1. 'MVNG1905' exhibits flowers that are relatively large in size that open pink and change to violet-purple in color.
2. 'MVNG1905' exhibits re-blooming throughout the season.
3. 'MVNG1905' exhibits a long flowering season that commences early in the season.
4. 'MVNG1905' exhibits a broadly spreading and slightly upright plant habit.

The female parent of 'MVNG1905' differs from 'MVNG1905' in having flowers that are larger in size, in commencing bloom earlier in the season, and in having a less dense plant habit. 'MVNG1905' can be most closely compared to the *Geranium* cultivars 'Max Frei' (not patented) and 'New Hampshire Purple' (not patented). 'Max Frei' is similar to 'MVNG1905' in plant habit and flower coloration. 'Max Frei' differs from 'MVNG1905' in having flowers that are smaller in size, in commencing bloom later in the season, and in having a less dense and less compact plant habit. 'New Hampshire Purple' is similar to 'MVNG1905' in plant height. 'New Hampshire Purple' differs from 'MVNG1905' in having flowers that are lighter in color and smaller in size, a shorter blooming season, and a less robust growth habit.

'MVNG1905' can also be compared to the co-pending cultivars of *Geranium*; 'MVNG1811' and 'MVNG1901'. 'MVNG1811' differs from 'MVNG1905' in having light pink flowers. 'MVNG1901' differs from 'MVNG1905' in having lighter violet-pink flowers.

BRIEF DESCRIPTION OF THE DRAWING

The accompanying color photograph illustrates the overall appearance and distinct characteristics of the new *Geranium*. The photograph was taken of a one year-old plant of 'MVNG1905' as grown outdoors in a 15-cm container in Warmond, The Netherlands.

The FIGURE provides a side view of 'MVNG1905' in bloom.

The colors in the photograph are as close as possible with the digital photography and printing techniques utilized and the color codes in the detailed botanical description accurately describe the colors of the new *Geranium*.

DETAILED BOTANICAL DESCRIPTION OF THE PLANT

The following is a detailed description of one year-old plants of the new cultivar as grown outdoors in a 15-cm circular container outdoors in Warmond, The Netherlands. The phenotype of the new cultivar may vary with variations in environmental, climatic, and cultural conditions, as it has not been tested under all possible environmental conditions. The color determination is in accordance with the 2015 6$^{th}$ edition Colour Chart of The Royal Horticultural Society, London, England, except where general color terms of ordinary dictionary significance are used.

General characteristics:

*Blooming period*.—Spring into late summer in The Netherlands.

*Plant type*.—Herbaceous perennial.

*Plant habit*.—Flattened, broadly spreading to slightly upright.

*Height and spread*.—Average of 11.7 cm in height and 40.5 cm in spread as a one year-old plant grown in a container, reaches 20 cm in height and 45 cm in width in the landscape.

*Hardiness*.—At least in U.S.D.A. Zones 5 to 9.

*Diseases and pests*.—No susceptibility or resistance to diseases or pests has been observed.

*Root description*.—Slightly fleshy, overall average diameter of the root system is 2 mm, both shallow and moderately deep distribution into the soil, moderate density, moderately branched, smooth and glabrous surfaces, 164C in color.

*Root development*.—Average of 6 to 8 weeks for root initiation, 12 to 14 weeks to produce a rooted cutting.

*Growth rate*.—Moderately vigorous.

*Propagation*.—Stem cuttings and tissue culture.

Branch description:

*Branch size*.—Average of 17.3 cm in length and 2 mm in width.

*Branch shape*.—Round.

*Branch strength*.—Moderately strong.

*Branch aspect*.—Average of 70°.

*Branch color*.—Young; 144A, mature; 144B, upper side of branches 174A to 174B.

*Branch surface*.—Slightly glossy and moderately covered with short hairs, average of 1.5 mm in length and too small to measure color.

*Internode length*.—Average of 2.3 cm.

*Branching habit*.—Freely branched, average of 13 main branches, 39 lateral branches.

Foliage description:

*Leaf shape*.—Reniform (overall shape), palmately cleft with an average of 5 lobes.

*Leaf division*.—Simple.

*Leaf base*.—Hastate, lobes free to touching.

*Leaf apex*.—Acute.

*Leaf venation*.—Palmate, upper surface 144B, lower surface 146B to 146C.

*Leaf margins*.—Lanciniate.

*Leaf lobes*.—Sinuses are deep, sinus orientation is divergent.

*Leaf attachment*.—Petiolate.

*Leaf arrangement*.—Opposite.

*Leaf surface*.—Both surfaces non-rugose, upper surface very slightly glossy, lower surface matte, covered with short hairs an average of 0.75 mm in length N155A in color.

*Leaf color*.—Young upper surface; 137B, young lower surface; 138A, mature upper surface; NN137A, mature lower surface; 147B.

*Leaf size*.—Average of 2.7 cm in length and 2.9 cm in width.

*Leaf quantity*.—Average of 16 (8 pairs) per lateral branch.

*Petioles*.—Average of 3 cm in length and 1 mm in width, upper and lower surface color 144B, both surfaces are slightly glossy, densely covered with short hairs an average of 1.25 mm in length and N155A, high strength.

*Stipules*.—2 leafy stipules, present at the base of the leaves, deltoid in shape, apex is cillate, broadly cuneate base, average of 4 mm in length, 3 mm in width, 150D in color.

Flower description:

*Inflorescence type*.—Axillary, solitary.

*Lastingness of flowers*.—Average of 7 days, self cleaning.

*Flowers*.—Up to 60 per plant, rotate, single, average of 4.4 cm in length and diameter, 1.2 cm in depth, primarily upward to outward, no fragrance.

*Flower bud*.—Up to 600 per plant, an average of 8 mm in length, 5 mm in width, color; 137C, axially striped 138C, obovate in shape, surface is densely covered with short glandular hairs an average of 0.1 mm in length, color; 137C, axially striped 138C.

*Petals*.—5, rotate in arrangement, 1 whorl, obovate to obcordate in shape, narrow cuneate base, broadly obtuse to broadly retuse apex, entire margins, surfaces are glabrous, velvety, and matte, average of 2.3 cm in length, 2.1 cm in width, color: when opening upper surface; NN78A, tinged margins; N81B, veins N78A, when opening lower surface; N78C to N78D, tinged margins 76A, when fully open upper surface; NN78A, tinged margins N81B, veins N78A, fading after maturity N81B, veins N78A, when fully open lower surface; N78C to N78D, tinged margins 76A, veins N77D, changing after maturity N81C, veins N77D.

*Calyx*.—Rotate, average of 6 mm in length and 1.9 cm in width.

*Sepals*.—Average of 5, broadly ovate in shape, entire margins, mucronate apex, cuneate base, average of 1.1 cm length, 4.5 mm in width, upper surface glabrous, smooth, moderately glossy, lower surface glabrous, smooth, matte and densely covered with short hairs 1 mm in length, N155A in color, color: when opening upper surface; 146D, margined, transparent 157A, veins 143A, when opening lower surface; 143B, margined, transparent 157A, veins 137B, when fully open upper surface; 146D, margined, transparent 157A, when fully open lower surface; 143B, margined, transparent 157A.

*Peduncles*.—Average of 7 cm in length and 1 mm in diameter, moderately to strong, held in a 30° angle to lateral branch, 144A to 144B in color, surfaces are slightly glossy and densely covered with short hairs, average of 0.75 mm in length and a blend of NN155D and 157D in color.

*Pedicels*.—None.

*Floral bracts*.—Two bracts are placed at the top of about half of the flowers, lanceolate in shape, average of 3.5 mm in length, 2 mm in width, entire margins, narrow acuminate apex, cuneate base, upper surface smooth and glabrous, lower surface and margins densely covered with short hairs average of 0.3 mm in length, both surfaces 146D in color, margins transparent 150D in color.

Reproductive organs:

*Gynoecium*.—Pistil; 1, average of 9 mm in length, stigmas; 5, curled, 2 mm in length, 6 mm in diameter, N170C in color, style; average of 8 mm in length, color; 164B, ovary; 147B in color.

*Androecium*.—Stamens; 10, anthers; narrow oblong in shape, 2 mm in length, 0.75 mm in width, N92D in color, filaments; 7 mm in length, 73C in color, base 157A in color, pollen; moderate in quantity, N187B in color.

*Fruit/seeds*.—None observed to date.

It is claimed:

1. A new and distinct cultivar of *Geranium* plant named 'MVNG1905' as herein illustrated and described.

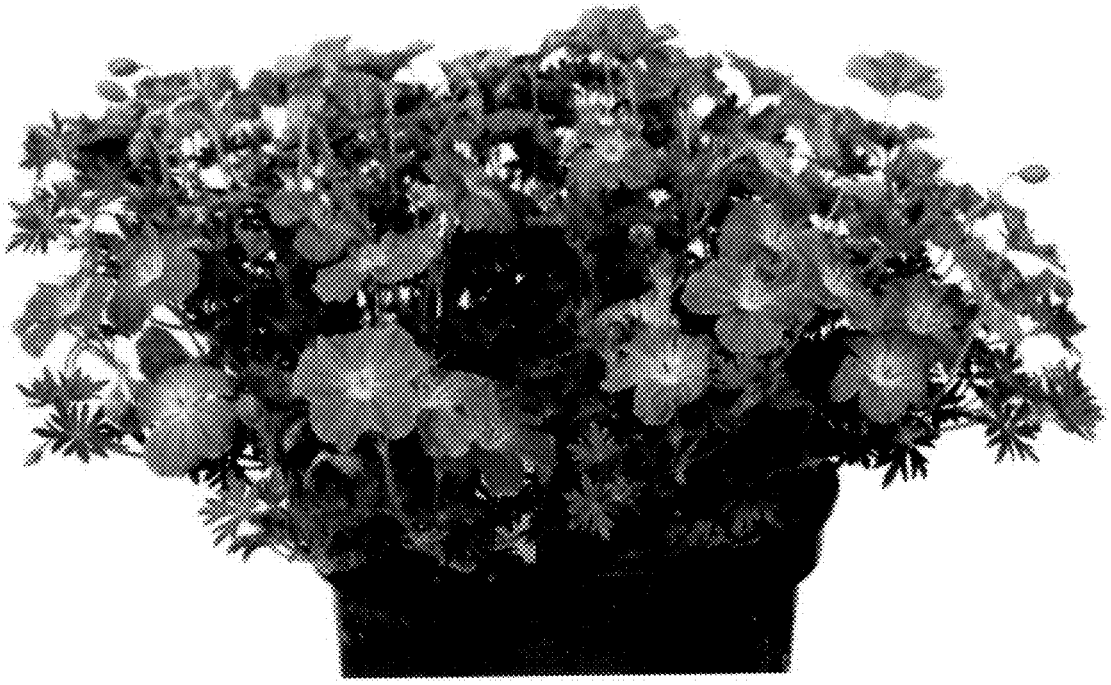

* * * * *